US00PP28417P2

(12) United States Plant Patent
Sato et al.

(10) Patent No.: US PP28,417 P2
(45) Date of Patent: Sep. 19, 2017

(54) **NEW GUINEA *IMPATIENS* PLANT NAMED 'SAKIMP041'**

(50) Latin Name: ***Impatiens×hybrida* hort**
Varietal Denomination: SAKIMP041

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,102

(22) Filed: Mar. 30, 2016

(51) Int. Cl.
*A01H 5/02* (2006.01)

(52) U.S. Cl.
USPC ..... Plt./318.4

(58) Field of Classification Search
USPC ..... Plt./318.4, 318.5, 318.6
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *Impatiens* plant particularly distinguished by having light purple flowers with white centers, and a compact habit, is disclosed.

2 Drawing Sheets

Genus and species: *Impatiens×hybrida* hort.
Variety denomination: 'SAKIMP041'.

BACKGROUND OF THE NEW PLANT

The present invention comprises a new and distinct variety of New Guinea *impatiens* plant, botanically known as *Impatiens×hybrida* hort, and referred to by the variety name 'SAKIMP041'. 'SAKIMP041' originated from an interspecific hybridization in Misato, Japan between the proprietary female *Impatiens* line 'H-10HA' (unpatented) and the proprietary male *Impatiens* line 'NH-214C-8HD' (unpatented).

In August 2011, the parental lines were crossed and a population of F1 plants was created. The F1 plants were evaluated in Misato, Japan in an open-field trial. The criteria for selection included bright flower color, compact habit, and strong root system. At the completion of the trial, one single plant selection was made based on the above criteria and vegetatively propagated and designated 'M2013-381'. From June to August 2013, the selection was evaluated in an open-field in Misato, Japan. Shoot-tip cuttings of the selection were then shipped to Salinas, Calif., where the plants were regenerated and re-evaluated for stability of traits. 'SAKIMP041' was found to reproduce true to type in successive generations of asexual propagation via shoot-tip cuttings in Salinas, Calif.

SUMMARY

The following are the most outstanding and distinguishing characteristics of this new variety when grown under normal horticultural practices in Salinas, Calif.

1. Light purple flowers with white centers; and
2. A compact habit.

DESCRIPTION OF THE PHOTOGRAPHS

This *Impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
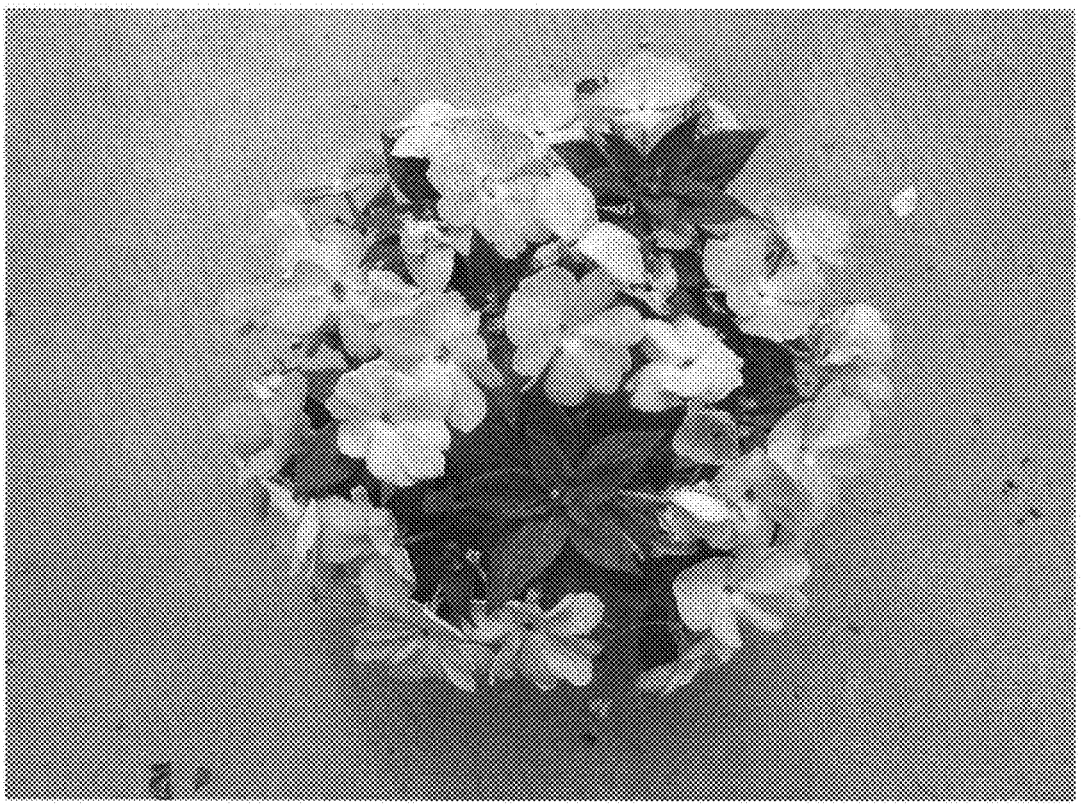
FIG. 1 shows the overall plant habit of the plant grown in a pot.
Figure 2:
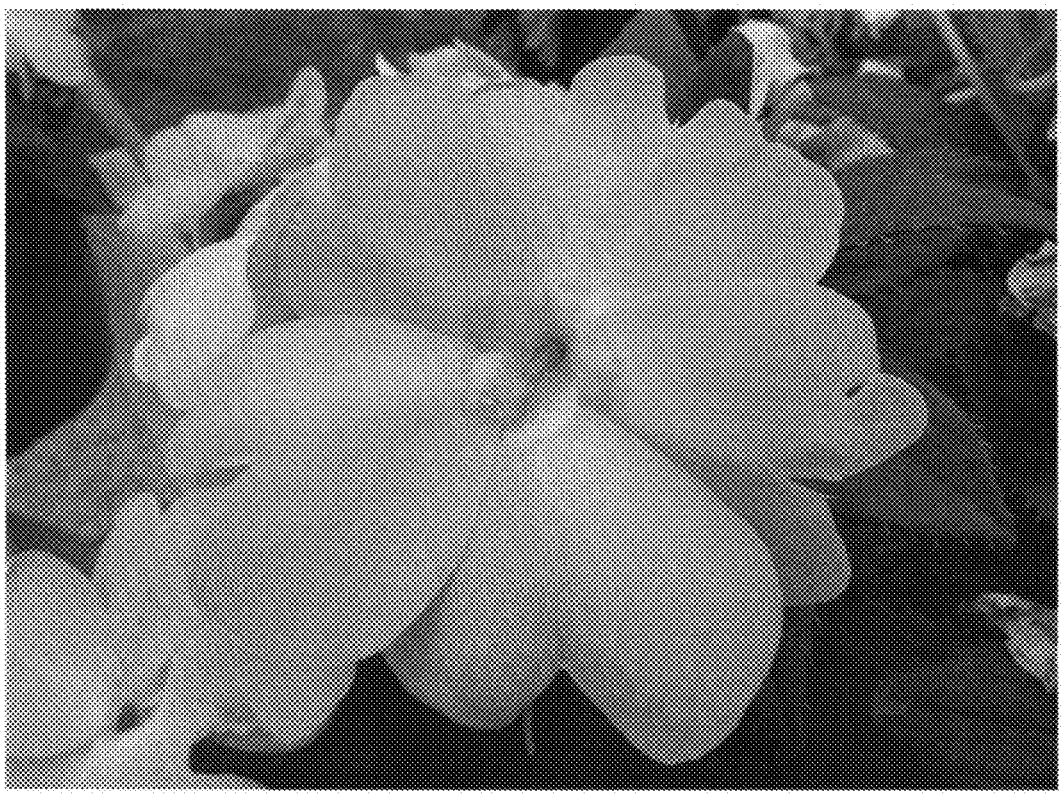
FIG. 2 shows a close-up of the mature inflorescence of the plant.

The following detailed descriptions set forth the distinctive characteristics of 'SAKIMP041'. Data was obtained from plants grown about 1 month from propagation by terminal cuttings in Salinas, Calif. under greenhouse conditions. Color references are to The Royal Horticultural Society of London color chart (R.H.S.), $4^{th}$ edition (2001). Anatomic labels are from *The Cambridge Illustrated Glossary of Botanical Terms*, by M. Hickey and C. King, Cambridge University Press.

Classification:

*Family*.—Balsaminaceae.
*Botanical*.—*Impatiens×hybrida* hort.
*Common*.—*Impatiens*.
*Designation*.—'SAKIMP041'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Parentage:

*Female parent*.—The proprietary *Impatiens* line 'H-10HA' (unpatented).

*Male parent*.—The proprietary *Impatiens* line 'NC-214C-8HD' (unpatented).

Plant description:

*Habit*.—Compact.

*Height*.—17.5 cm from the soil line to the top of the foliage.

*Spread*.—26.0 cm.

*Number of branches per plant*.—11 total with 10 main branches.

*Length of branches*.—1.5 cm from the soil line to the first node, 7.5 cm total.

*Diameter of branches*.—2.0 cm for the main branch; 0.7 cm to 1.0 cm for the other secondary branches.

*Color of branches*.—RHS 146A (Yellow).

*Life cycle*.—Annual.

*Time to produce a rooted cutting*.—About 4 weeks.

*Time to bloom from propagation*.—6 to 8 weeks.

*Flowering requirements*.—Will flower so long as the temperature is above 5° C.

*Temperature tolerances*.—Plants observed to continue flowering in a temperature range of 5° C. to 36° C.

Stems:

*Color*.—Closest to RHS 146C (Yellow-green).

*Anthocyanin color*.—Absent.

*Pubescence*.—Absent.

*Description*.—Strong; circular in cross-section, smooth and shiny.

*Length*.—3.0 cm to 5.0 cm from the first node to the second node; 7.5 cm to 10.0 cm total.

*Diameter*.—5.0 mm.

*Internode length*.—2.0 cm.

Leaves:

*Arrangement*.—Whorled with up to 5 leaves per node, opposite if only two leaves at one node.

*Shape*.—Lanceolate, curled.

*Apex*.—Acuminate.

*Base*.—Shortly attenuate.

*Margin*.—Serrate.

*Surface appearance*.—Dull, waxy.

*Length*.—5.4 cm.

*Width*.—2.5 cm.

*Color*.—Upper surface: RHS 139A (Green). Lower surface: RHS 147B (Yellow-green).

*Variegation*.—Absent.

*Fragrance*.—Absent.

*Pubescence*.—Absent.

*Petiole*.—Length: 6.0 mm. Diameter: 3.0 mm. Color: Closest to RHS 145C (Yellow-green). Texture: Smooth, glabrous.

*Venation pattern*.—Pinnate.

*Venation color*.—Upper surface: RHS 145D (Yellow-green). Lower surface: Closest to RHS 138B (Green).

Flowers:

*Number of flowers per node*.—1 to 3 in bloom at one time; about 10 flower buds.

*Number of flowers per plant*.—Approximately 65 in bloom.

*Lastingness of individual flowers on the plant*.—14 days.

*Flower type*.—Single flower with spur.

*Fragrance*.—Absent.

Corolla:

*Shape*.—Roughly circular with 5 radial petals.

*Diameter*.—5.5 cm.

*Depth*.—1.0 cm.

*Petals*.—Pubescence (both surfaces): Glabrous. Length: 3.2 cm. Width: 2.8 cm. Shape: Obcordate. Apex: Emarginate (cleaved). Base: Attenuate. Margin: Entire. Color: Upper surface: Closest to RHS N78 (Purple). Lower surface: Closest to RHS 77D (Purple). Eye zone: RHS 155C (White).

Calyx:

*Sepals*.—Shape: Lanceolate. Number per flower: 2. Color: Upper surface: Closest to RHS 145A (Yellow-green) with slight RHS 145D (Yellow-green) at the base and RHS 144B (Yellow-green) at the tip. Lower surface: RHS 145C (Yellow-green) with slight RHS 145D (Yellow-green) at the base and RHS 144B (Yellow-green at the tip). Length: 1.3 cm. Width: 6.0 mm. Apex: Caudate. Base: Subcordate. Margin: Entire. Texture (both surfaces): Glabrous.

Bud:

*Surface texture*.—Glabrous.

*Length*.—1.8 cm.

*Diameter*.—1.2 cm.

*Shape*.—Deltoid longitudinal in cross-section.

*Color*.—Closest to RHS N74D (Red-purple) with RHS 144B (Yellow-green) at the edge.

Peduncle:

*Length*.—2.9 cm.

*Color*.—RHS 145B (Yellow-green) with slight RHS 145A (Yellow-green) at either end.

*Diameter*.—2.0 mm.

*Texture*.—Smooth, glabrous.

Spur:

*Color*.—Closest to RHS 157B (Green-white) with slight RHS N144C (Yellow-green) at the tip and the base. Also slight RHS 77 (Purple) at the base.

*Shape*.—Tubular, curved downward.

*Length*.—5.5 cm.

*Diameter*.—1.0 mm to 2.0 mm.

Reproductive organs:

*Stamen form*.—Fused, split into 4 lobes.

*Stamen number*.—5.

*Filament form*.—Free.

*Anther length*.—6.0 mm.

*Anther color*.—Closest to RHS 70B but transparent.

*Pistil number*.—1.

*Stigma color*.—Closest to RHS 145D (Yellow-green).

*Style color*.—RHS 144A (Yellow-green).

*Ovary arrangement*.—Parietal.

*Ovary interior color*.—RHS 145B (Yellow-green).

*Pollen amount*.—Abundant.

*Pollen color*.—RHS 158B (Yellow-white).

*Pollen description*.—Powdery.

*Seed production*.—Not observed.

Disease and insect resistance: No particular resistance or susceptibility observed.

COMPARISON WITH PARENTAL LINES AND COMMERCIAL VARIETY

'SAKIMP041' is distinguished from its parents as shown in Table 1 below:

TABLE 1

Comparison with Parental Lines

| Characteristic | 'SAKIMP041' | Female Parent 'H-10HA' | Male Parent 'NH-214C-8HD' |
|---|---|---|---|
| Flower color | Orchid (light purple) | White | Orchid but more pink |
| Plant growth habit | Compact | More compact than 'SAKIMP041' | More vigorous than 'SAKIMP041' |

When 'SAKIMP041' compared to the commercial *Impatiens* variety 'SAKIMP006' (U.S. Plant Pat. No. 19,501), the following differences are as described in Table 2 below.

TABLE 2

Comparison with Similar Variety

| Characteristic | 'SAKIMP041' | 'SAKIMP006' |
|---|---|---|
| Growth habit | Compact | Vigorous |
| Petal color, upper surface | Closest to RHS N78 (Purple) | RHS N74B (Red-purple) |
| Spur color | Closest to RHS 157B (Green-white) with slight RHS N144C (Yellow-green) at the tip and the base. Also slight RHS 77 (Purple) at the base. | Greyed-purple |
| Bud color | Closest to RHS N74D (Red-purple) with RHS 144B (Yellow-green) at the edge | RHS N74C (Red-purple) with RHS 185B (Greyed-purple) at the edge |

We claim:

1. A new and distinct variety of New Guinea *Impatiens* plant named 'SAKIMP041' as described and illustrated herein.

* * * * *